United States Patent
Radke et al.

(10) Patent No.: US 8,986,729 B2
(45) Date of Patent: *Mar. 24, 2015

(54) PALATABLE SUSPENDING VEHICLE FOR PHARMACEUTICAL INGREDIENTS

(71) Applicant: Fagron, Inc., St. Paul, MN (US)

(72) Inventors: Joshua Radke, Eagan, MN (US); Michael Jones, Rosemount, MN (US); Martin Erickson, Apple Valley, MN (US)

(73) Assignee: Fagron, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/034,198

(22) Filed: Sep. 23, 2013

(65) Prior Publication Data

US 2014/0187628 A1 Jul. 3, 2014

Related U.S. Application Data

(63) Continuation of application No. 13/207,849, filed on Aug. 11, 2011, now Pat. No. 8,541,018, which is a continuation of application No. 11/203,520, filed on Aug. 12, 2005, now Pat. No. 8,021,682.

(60) Provisional application No. 60/601,326, filed on Aug. 13, 2004.

(51) Int. Cl.
*A61K 47/00* (2006.01)
*A61K 47/36* (2006.01)
(Continued)

(52) U.S. Cl.
CPC .............. *A61K 47/36* (2013.01); *A61K 9/0095* (2013.01); *A61K 9/10* (2013.01); *A61K 31/166* (2013.01); *A61K 31/192* (2013.01);
(Continued)

(58) Field of Classification Search
None
See application file for complete search history.

(56) References Cited

U.S. PATENT DOCUMENTS 4,008,116 A 2/1977 Sebel
6,180,159 B1 1/2001 Villigran et al.
(Continued)

OTHER PUBLICATIONS

Allen, L. V. Jr., 1998, *The Art, Science, and Technology of Pharmaceutical Compounding*, American Pharmaceutical Association, Washington, D.C., p. 168-169.
Allen, L. V. Jr., 2002, *The Art, Science, and Technology of Pharmaceutical Compounding*, American Pharmaceutical Association, Washington, D.C., p. 251 "Suspensions".
(Continued)

*Primary Examiner* — Anand Desai
*Assistant Examiner* — Melissa Mercier
(74) *Attorney, Agent, or Firm* — Bryan Cave LLP

(57) ABSTRACT

The invention relates to a liquid vehicle that can be used to create suspensions and/or solutions of liquid or powdered medications. The vehicle is thixotropic and has improved stability and rheologic characteristics. Vehicles of the invention include an aqueous medium and a suspending agent comprising a polysaccharide having at least 50% glucose repeating saccharide units and at least 90% alpha linkages. The polysaccharide can be a starch, modified starch, or glycogen. The aqueous medium and individual components of the vehicle provide a palatable and easily ingested drug preparation. The invention also provides a vehicle containing an aqueous medium, suspending agent comprising a polysaccharide having at least 50% glucose repeating saccharide units and at least 90% alpha linkages, buffer, and artificial sweetener, the combined suspending vehicle having a pH of about 3 to about 10 and an osmolality of 300 mOmsol or less.

19 Claims, 4 Drawing Sheets

(51) Int. Cl.
| | |
|---|---|
| A61K 9/00 | (2006.01) |
| A61K 9/10 | (2006.01) |
| A61K 31/166 | (2006.01) |
| A61K 31/192 | (2006.01) |
| A61K 31/197 | (2006.01) |
| A61K 31/277 | (2006.01) |
| A61K 31/325 | (2006.01) |
| A61K 47/12 | (2006.01) |
| A61K 47/26 | (2006.01) |
| A61K 47/34 | (2006.01) |

(52) U.S. Cl.
CPC ............ *A61K 31/197* (2013.01); *A61K 31/277* (2013.01); *A61K31/325* (2013.01); *A61K 47/12* (2013.01); *A61K 47/26* (2013.01); *A61K 47/34* (2013.01)
USPC .......................................... 424/439; 424/400

(56) References Cited

U.S. PATENT DOCUMENTS

| | | | |
|---|---|---|---|
| 6,238,695 | B1 | 5/2001 | Makooi-Morehead et al. |
| 6,475,539 | B1 | 11/2002 | DeWille et al. |
| 6,664,287 | B2 | 12/2003 | Avery et al. |
| 7,018,668 | B2 | 3/2006 | Villagran et al. |
| 8,541,018 | B2 * | 9/2013 | Radke et al. ................. 424/439 |
| 2004/0258716 | A1 | 12/2004 | Gao et al. |
| 2005/0208141 | A1 | 9/2005 | Farber et al. |
| 2006/0034873 | A1 | 2/2006 | Radke et al. |
| 2006/0034947 | A1 | 2/2006 | Burr |

OTHER PUBLICATIONS

Allen, L. V. Jr., Jan./Feb. 2001, *International Journal of Pharmaceutical Compounding*, 5(1) "Featured Excipient: Oral Liquid Vehicles".
Allen, L. V. Jr., Jul./Aug. 2001, *International Journal of Pharmaceutical Compounding*, 5(4) "Basics of Compounding: Suspensions".
Allen, L. V. Jr., Nov./Dec. 1999, *International Journal of Pharmaceutical Compounding*, 3(6):479-486 "Featured Excipient: Viscosity-Increasing Agents for Aqueous Systems".
Ansel et al., 1999, *Pharmaceutical Dosage Forms and Drug Delivery Systems*, 7th ed., Lippincott Williams & Wilkins, Philadelphia, PA, Ch. 13, p. 346-364 "Disperse Systems".
Chan, D. S., Jan./Feb. 2001, *International Journal of Pharmaceutical Compounding*, 5(1) "Stability Issues for Compounding Extemporaneously Prepared Oral Formulations for Pediatric Patients".
International Search Report mailed Feb. 22, 2006.
Genarro, A. R., ed., 2000, *Remington: The Science and Practice of Pharmacy*, 20th ed., Lippincott Williams & Wilkins, Philadelphia, PA, pp. 744, 321.
Hegenbart et al., *Understanding Starch Functionality*, Food Prodict Design, Jan. 1996.
Hegenbart, *Understanding Starch Functionality*, Food Product Design, Jan. 1996, pp. 1-6.
International Journal of Pharmaceutical Compounding, Mar./Apr. 1997, *International Journal of Pharmaceutical Compounding*, 1(2):84-86 "Compounding for the Pediatric Patient".
Meyer and Cohen, 1959, *The Journal of the Society of Cosmetic Chemists*, 10(1):143-154 "The Rheology of Natural and Synthetic Hydrophilic Polymer Solutions as Related to Suspending Ability".
Miller, 1983, *The Pharmaceutical Journal*, Nov. 26, 1983, p. 629-631 "Frontline pharmacist".
Palmer, H. A., Jan./Feb. 1998, *International Journal of Pharmaceutical Compounding*, 2(1) "Extemporaneous Lozenge Formulations".
Seeley et al. and Allen et al., eds., 1992, *Anatomy & Physiology*, 2nd ed., Mosby-Year book Inc., St. Louis, MO, p. 863.
Thompson and Davidow, 2004, *A Practical Guide to Contemporary Pharmacy Practice*, Lippincott Williams & Wilkins, Baltimore, MD, Ch. 28, pp. 28.1 "Suspensions".
Thompson and Davidow, 2004, *A Practical Guide to Contemporary Pharmacy Practice*, Lippincott Williams & Wilkins, Baltimore, MD, Ch. 28, pp. 28.1-28.23 "Suspensions".
United States Pharmacopeial Convention, Inc., 2004, *USP 27th ed., The United States Pharmacopeia—NF 22nd ed., The National Formulary*, United States Pharmacopeial Convention, Inc., Rockville, MD, p. 2945.

* cited by examiner

PALATABLE SUSPENDING VEHICLE FOR PHARMACEUTICAL INGREDIENTS

This application is a continuation of U.S. application Ser. No. 13/207,849, filed Aug. 11, 2011, now U.S. Pat. No. 8,541, 018, which is a continuation of U.S. application Ser. No. 11/203,520, filed Aug. 12, 2005, now U.S. Pat. No. 8,021,682 which claims priority under 35 U.S.C. §119(e) to U.S. Provisional Application Ser. No. 60/601,326, filed on Aug. 13, 2004, which are hereby incorporated by reference in their entirety.

FIELD OF THE INVENTION

The invention relates to a liquid vehicle that can be used to create suspensions and/or solutions of a solid or liquid medicament. The vehicle is adapted for easy blending, finished product stability, and safety.

BACKGROUND OF THE INVENTION

There is often a need to administer solid medications in oral liquid forms to patients. These patients include adults who cannot swallow solid dosage forms, infants and children, nonambulatory patients with nasogastric tubes, geriatric patients, and animals. In a typical preparation, a medication available in a tablet or bulk powder form is finely ground, wetted with a wetting agent, and then combined slowly with a liquid vehicle. This technique is flexible and provides a method to treat a patient with a variety of medicaments in alternative dosage forms.

Ideally, a liquid suspending vehicle is thixotropic, has a measurable yield value or is a pseudoplastic power law liquid with a low flow index, is shear thinning, prevents solid particles too large to be suspended from forming a hard cake in the vehicle, is physiologically compatible and results in minimal gastric impact, is resistant to changes induced by the addition of unknown chemical substances, provides a chemically inert environment, and has a pleasant or neutral flavor and mouth-feel (Thompson, J. E., *A Practical Guide to Contemporary Pharmacy Practice*, Lippincott Williams & Wilkins, Baltimore, Md., 1998, p. 28.1). There are a variety of products currently available whose primary function is to serve as a liquid vehicle for compounding extemporaneous solutions or suspensions. None of the currently available products meet all of the criteria set forth in Thompson (Id.).

Most products currently available employ one or more suspending agents, such as agar, alginic ac, activated attapulgite, bentonite, carbomer, carboxymethycellulose (calcium and sodium salts), carrageenan, microcrystalline cellulose, dextrin, gelatin, guar gum, hydroxypropylmethylcellulose, methylcellulose, pectin, poloxamer, polyoxyethylene oxide, polyvinyl alcohol, povidone, propylene glycol alginate, silicon dioxide, sodium alginate, tragacanth, and xanthan gum (Allen, L. V. Jr., *The Art, Science, and Technology of Pharmaceutical Compounding*, American Pharmacy Association, Washington, D.C., 1998, p. 169).

While these products are designed to provide permanent suspensions, they suffer from shortcomings including: sedimentation of ingredients added to the suspension; difficulty resuspending sedimented ingredients; hydrolysis of the suspending agent; deactivation, precipitation, or coagulation of the suspending agent due to chemical, electrolyte, or cation sensitivities and/or physical changes such as shear or temperature; and deactivation, precipitation, or coagulation by amphiphilic or detergent-like molecules. In addition, many of the previously formulated liquid suspending vehicles are hyperosmotic, incompatible with one or more frequently compounded medications, and/or have a bulk laxative effect.

Clearly, a substantial need exists for an improved liquid vehicle for preparing medicinal suspensions or solutions.

BRIEF DISCUSSION OF THE INVENTION

The invention relates to a liquid vehicle that can be used by a pharmacist, physician, dentist, veterinarian, or other health professional to suspend, dissolve, or disperse a drug to provide a liquid suspension suitable for human or animal ingestion. The vehicles of the invention can serve as the basis for a palatable and safe compounded or manufactured medicinal preparation.

A vehicle of the invention typically contains an aqueous medium and a suspending agent comprising a polysaccharide having at least 50% glucose repeating saccharide units and at least 90% alpha linkages. Such suspending agents typically include starch, modified starch, or glycogen. In an embodiment, the vehicle comprises about 1% to about 15% suspending agent by weight.

Some embodiments of the invention contain buffers, sweeteners, preservatives, antimicrobial agents, anti-oxidants, flavoring agents, flavor enhancers, colorants, texture modifiers, surfactants, and/or defoaming agents. The sweetener can be a nutritive or non-nutritive artificial sweetener. Examples of suitable artificial sweeteners include sucralose, saccharin, aspartame, stevia, and acesulfame K. In an embodiment, a vehicle of the invention comprises about 1% or less artificial sweetener by weight. A vehicle of the invention can be unbuffered or buffered to a pH of about 3 to 10. In some embodiments, the pH of the vehicle is buffered to mimic the pH of the stomach.

In an embodiment, a vehicle of the invention contains an aqueous medium, suspending agent comprising a polysaccharide having at least 50% glucose repeating saccharide units and at least 90% alpha linkages, an artificial sweetener, and a buffer. The suspending agent can contain a modified or unmodified starch and the pH of the vehicle can be from about 3 to about 10.

The vehicles of the invention are compatible with most drugs administered orally. A drug in powder form or pill, capsule, or other solid drug product can be rendered into a fine powder form and combined with a vehicle of the invention. Vehicles of the invention can be combined with about 0.01 to about 100,000 mg of drug or inactive ingredient per each 100 ml of vehicle. Typical concentrations are from about 1 to about 100 mg of drug per ml of vehicle.

The vehicles of the invention have improved rheological characteristics and stability. Preferably, a vehicle of the invention is thixotropic, and has a yield value greater than 0 or, at shear rates less than about 1 $\sec^{-1}$, the flow index of the vehicle decreases or remains constant as the shear rate decreases. In an embodiment, the vehicle has a yield value of about 0.01 dynes/cm$^2$ to about 600 dynes/cm$^2$. A vehicle of the invention can maintain its form and suspending function after chemical or physical perturbation. A vehicle of the invention can tolerate a variety of perturbations including, but not limited to, changes in ionic strength, Lewis acidity/basicity of added ingredients; physical conditions of preparation including shearing, freezing and heating, the presence of metals and/or chelating agents, and the presence of soap, soap-like, or detergent type molecules. Embodiments of the invention allow for easy and quick resuspension of sedimented ingredients. In an embodiment, a drug or inactive ingredient can be suspended or resuspended in a vehicle of the invention without high shear mixing.

The osmolality, pH, and carbohydrate or natural sweetener content can be controlled in a vehicle of the invention to maintain physiological compatibility with a patient. Hyperosmotic preparations (preparations with osmolality greater than 300 mOsmol) can induce saline laxation in a patient which results in some level of dehydration for the patient. Infants, small children, and the elderly are most sensitive to this dehydration.

Embodiments of the invention can be formulated with very low osmolality. This aspect of the invention enables a compounding pharmacist, for example, to add drugs and/or inactive ingredients in significant concentrations without concern about hypertonicity in the final preparation. A vehicle of the invention can be formulated with an osmolality of about 300 mOsmol or less. In an embodiment, the osmolality of the vehicle is 50 mOsmol or less. In another embodiment, the osmolality of the vehicle is about 30 to about 40 mOsmol. In yet another embodiment, the osmolality of a vehicle of the invention is sufficiently low such that the osmolality of the final preparation does not exceed 300 mOsmol after addition of a drug(s) and inactive ingredients.

DETAILED DESCRIPTION OF THE INVENTION

Figure 1:
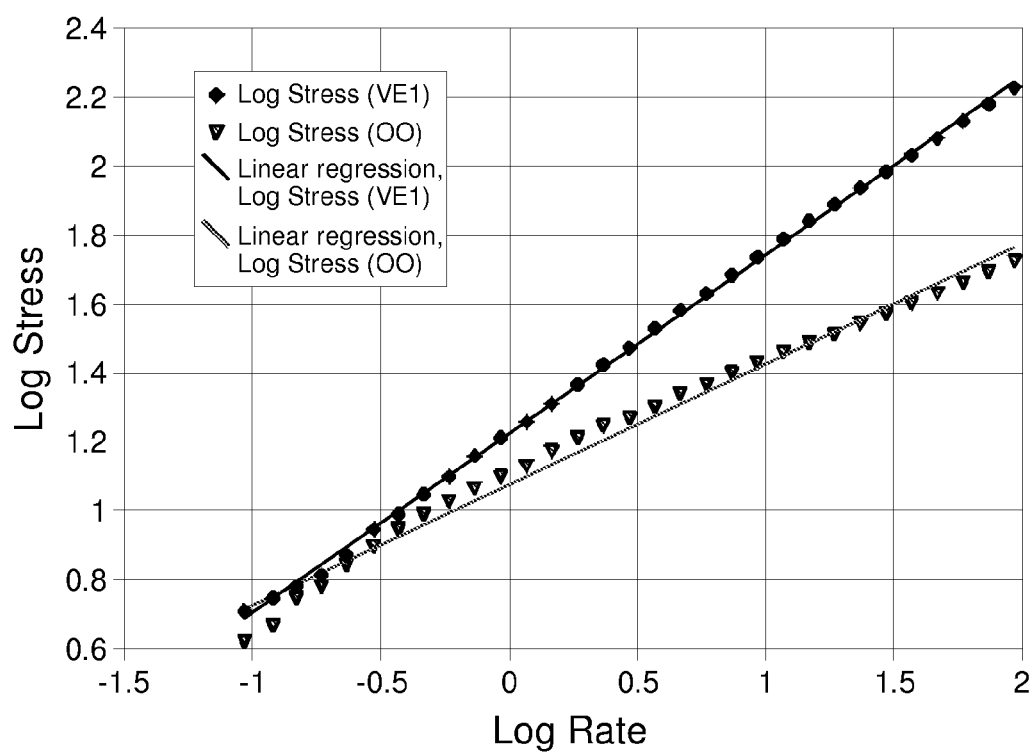
FIG. 1 shows shear stress of an embodiment of the invention (VE1) and a 1:1 mixture of ORA-SWEET SF® and ORA-PLUS® (OO) at shear rates from 0.1 to 100.

The invention relates to aqueous vehicles that can be used to suspend, dissolve, or disperse a liquid or solid medicament. The term "medication", "medicament", or "drug" as used herein means a product intended for use in the diagnosis, cure, mitigation, treatment, or prevention of a disease in a human or animal. Over-the-counter and prescription drugs, medications, or medicaments including, but not limited to, vitamins, cold medications, allergy medications, herbal medications, analgesics, pharmaceuticals, pharmaceutical compounds, active and inactive pharmaceutical ingredients, and nutriceuticals are included within the scope of the term "drug." A drug or drug product can be in liquid form, powder form, or solid form including, but not limited to, pills, tablets, and capsules. In some embodiments, the drug, medication, or medicament, is a solid or liquid oral dosage form. In a typical preparation, a medication available in a tablet or bulk powder form is finely ground, wetted with a wetting agent, and then combined slowly with a liquid vehicle. This technique is flexible and provides a method with which to administer a variety of medicaments orally in an alternative dosage form, such as a liquid, to patients.

A. Formulations and Rheology

An agent that can effectively suspend a drug, medication, or medicament into the vehicle is used to formulate the vehicles of the invention. A vehicle of the invention includes an aqueous medium and a suspending agent comprising a polysaccharide having at least 50% glucose repeating saccharide units and at least 90% alpha linkages. Surprisingly, we have found that an aqueous vehicle comprising such a suspending agent displays superior rheologic characteristics compared with previously formulated suspending vehicles containing cellulosic-based suspending agents. Suspending agents comprising a polysaccharide having at least 50% glucose repeating saccharide units and at least 90% alpha linkages typically include starch or glycogen. The starch can be unmodified or modified. In an embodiment, the balance of the polysaccharide comprises a $C_6$ saccharide unit.

In an embodiment, the vehicle comprises about 1% to about 15% suspending agent by weight. In another embodiment, the vehicle comprises about 2% to about 10% suspending agent by weight. In another embodiment, the vehicle comprises about 2% to about 7% suspending agent by weight. In yet another embodiment, the vehicle comprises about 4% to about 6% suspending agent by weight.

A number of references have tabulated pharmaceutical suspending agents; however, none of these references discloses starch as a suspending agent (*USP/NF: The Official Compendia of Standards*, $27^{th}$ and $22^{nd}$ eds., United States Pharmacopeial Convention, Inc., Rockville, Md., 2004.; Thompson, J. E., Davidow L., *A Practical Guide to Contemporary Pharmacy Practice*, $2^{nd}$ ed., Lippincott Williams & Wilkins, Baltimore, Md., 2004, p. 28.1-28.23; Allen, L. V. Jr., *The Art, Science, and Technology of Pharmaceutical Compounding*, $2^{nd}$ ed., American Pharmacy Association, Washington, D.C., 2002, p. 251; *Remington: The Science and Practice of Pharmacy*, Genarro A. R. ed., $20^{th}$ ed., Lippincott Williams &Wilkins, Philadelphia, Pa., 2000, pp. 744, 321; Allen, L. V. Jr., *Int. J. Pharm. Comp.*, 2001, 5:294; Allen, L. V. Jr., *Int. J. Pharm. Comp.*, 2001, 5:65; Chan, D. S., *Int. J. Pharm. Comp.*, 2001, 5:9; *Int. J. Pharm. Comp.*, 1997, 2:86; Palmer, H. A., *Int. J. Pharm. Comp.*, 1998, 2; Allen, L. V. Jr., *Int. J. Pharm. Comp.*, 1999, 3:479; Ansel H. C., Allen L. V. Jr., Popovich N. G., *Pharmaceutical Dosage Forms and Drug Delivery Systems*, $7^{th}$ ed., Lippincott Williams & Wilkins, Philadelphia, Pa., 1999, p. 346).

In an embodiment, the suspending agent is comprised of starch. Starch is a well-known material used in a variety of nutritive and non-nutritive applications. Starches can be obtained from a variety of plant sources including grains (such as wheat, corn, or rice), roots and tubers (such as tapioca, potato, and cassava), and fruits and vegetables (such as banana, tomato, and pumpkin). The nature of the starch materials from each individual plant source can exhibit different properties. Starches tend to be dispersible or suspendable in aqueous liquids to provide thickening properties. Since colloidal properties of starch and modified starches are primarily nonionic, the electrolytic sensitivity is lower than other common formulations, and in particular, charged versions of modified cellulosic suspending agents.

The starch can be derivatized or modified. The starch can be modified by crosslinking, substitution, hydrolysis, or dextrination. In an embodiment, modification includes capping the dangling hydroxy groups to form ethers or esters. Modified starches include, but are not limited to, starch acetate, starch phosphate, starch succinate, hydroxy ethyl starch, hydroxy propyl starch, cationic starches, oxidized starches and dextrin compositions. Preferred starches for use in the vehicles of the invention include modified starches that provide substantial thickening characteristics to enable the liquid vehicles of the invention to maintain a drug, medication, or medicament in suspension and modified starches that are compatible with the pH and osmolality of the desired end product.

In an embodiment, the vehicle comprises about 1% to about 15% starch or modified starch by weight. In another embodiment, the vehicle comprises about 2% to about 10% starch or modified starch by weight. In another embodiment, the vehicle comprises about 2% to about 7% starch or modified starch by weight. In yet another embodiment, the vehicle comprises about 4% to about 6% starch or modified starch by weight. In some embodiments, the starch is granular. In these embodiments, the granules can comprise a diameter of about 1 μm to about 150 μm.

In an embodiment, the starch comprises an amylose:amylopectin ratio of about 10%:90% to about 60%:40% by weight. In another embodiment, the starch comprises an amylose:amylopectin ratio of about 15%:80% to about 40%:60% by weight. In yet another embodiment, the starch comprises an amylose:amylopectin ratio of about 20%:80% to about 30%:70% by weight.

In an embodiment, the starch comprises a molecular weight of about 1 kD to about 10,000 kD. In another embodiment, the starch comprises a molecular weight of about 1,000 kD to about 10,000 kD. In another embodiment the starch comprises a molecular weight of about 2,000 kD to about 8,000 kD. In another embodiment, the starch comprises a molecular weight of about 3,000 kD to about 5,000 kD. In another embodiment, the starch comprises a molecular weight of about 20 kD to about 1,000 kD. In yet another embodiment, the starch comprises a molecular weight of about 20 kD to about 600 kD.

Manufacturers of natural and modified starches useful in the aqueous suspending vehicles of the invention include, but are not limited to, Cargill (Minneapolis, Minn.), National Starch and Chemical (Bridgewater, N.J.), Grain Processing Corporation (Muscatine, Iowa), Penford Food Ingredients (Englewood, Colo.), and A. E. Staley Manufacturing Company (Decatur, Ill.). Others manufacturers are known. The starch can be a food grade, reagent grade, ACS grade, pharmaceutical grade, or other suitable grade starch. Trade names of starches for use in vehicles of the invention include, but are not limited to, Inscosity 658 (Grain Processing Corporation, Muscatine, Iowa), Pure-Set B950 and B965 (Grain Processing Corporation, Muscatine, Iowa), Pure-Gel B992 and B994 (Grain Processing Corporation, Muscatine, Iowa), and STA-Rx (A. E. Staley Manufacturing Company (Decatur, Ill.). Other natural and modified starches are known.

One review reveals that the primary design goal of aqueous vehicles is to obtain a permanent suspension (see Meyer and Cohen, *J. Soc. Cosmetic Chemists*, 1959, 10:143; Miller, *Pharm. J.* Nov. 26, 1983, p. 629). In order for a suspension of a medicament to be considered permanent, suspended solid particles cannot visibly settle on the timescale of the evaluation. There are several mechanisms by which this can be accomplished. An aqueous vehicle can, for example, be thixotropic (the viscosity of the vehicle increases at rest), have a yield value, or be a pseudoplastic power law fluid having high viscosity at sedimentation shear rates.

A suspending vehicle of the invention preferably is thixotropic (the viscosity of the vehicle increases at rest), and has a yield value greater than 0 or is a pseudoplastic power law fluid. In an embodiment, the suspending vehicle is thixotropic and has a yield value greater than 0. The yield value can be from about 0.01 dynes/cm$^2$ to about 600 dynes/cm$^2$, from about 1 dynes/cm$^2$ to about 600 dynes/cm$^2$, from about 0.01 dynes/cm$^2$ to about 300 dynes/cm$^2$, from about 0.01 dynes/cm$^2$ to about 200 dynes/cm$^2$, from about 0.01 dynes/cm$^2$ to about 100 dynes/cm$^2$, from about 0.01 dynes/cm$^2$ to about 50 dynes/cm$^2$, or from about 0.01 dynes/cm$^2$ to about 10 dynes/cm$^2$. In an embodiment, the yield value is greater than 0 but equal to or less than 600 dynes/cm$^2$.

In another embodiment, the suspending vehicle is thixotropic and a pseudoplastic power law fluid. A power law fluid behaves in a predictable way with respect to well-defined shear rate and shear stress. The viscosity of a substance is given by $\eta = \tau \dot\gamma$, where $\eta$ is viscosity (in units of poise), $\tau$ is shear stress (in units of dynes/cm$^2$), and $\dot\gamma$ is shear rate (in units of sec$^{-1}$). Over some range of shear rate value, the shear stress (and indirectly the viscosity) of a power law fluid is given by $\tau = kD^n$, where k is known as the consistency index, D is the shear rate, and n is the flow index. A power law fluid with a higher consistency index will have a greater viscosity at a given shear rate. In an embodiment, a vehicle of the invention comprises a consistency index from about 400 to about 30,000 centipoise.

Power law fluids with flow indexes of less than 1 are pseudoplastic. For these fluids, the closer the flow index is to zero, the greater the viscosity becomes at low shear rates. There are two ranges of shear rates that are of primary interest for an aqueous suspending vehicle: 1) shaking and pouring of the vehicle are rheological events generating shear rates of about 10$^1$ to 10$^3$ sec$^{-1}$, and 2) sedimentation (settling of solid particles from suspension) generates shear rates of about 10$^{-6}$ to 10$^{-4}$ sec$^{-1}$. In some embodiments, at a shear rate of less than about 1 sec$^{-1}$, the flow index of a vehicle of the invention decreases or remains constant as the shear rate decreases. In an embodiment, a vehicle of the invention comprises a flow index of less than about 0.8 at a shear rate of less than about 1 sec$^{-1}$.

A suspending vehicle of the invention can be buffered or unbuffered. Preferably the buffer is generally recognized as safe (GRAS) by the U.S. Food and Drug Administration. The pH of the liquid vehicle of the invention can be adjusted to a physiological pH by measuring the pH of a batch of the material and either adding acid to lower pH or adding base to raise pH. The buffer can include an organic acid, inorganic acid, or salts thereof. Examples of suitable acids include, but are not limited to, malic acid, citric acid, ascorbic acid, tartaric acid, adipic acid, lactic acid, fumaric acid, maleic acid, acetic acid, phosphoric acid, or salts thereof, singly or in combination. Examples of suitable bases include, but are not limited to, calcium and sodium carbonate, calcium and sodium bicarbonate, and salts of the organic or inorganic acids listed above. The above listed compatible acids can be used for pH reduction; however, the increase in pH can be obtained through the use of small amounts of food grade inorganic bases including, but not limited to, metal hydroxides or basic salts thereof including sodium hydroxide solution, potassium hydroxide solution, ammonium hydroxide solution, ammonium chloride solution, sodium citrate, sodium dihydrogen phosphate, etc. Such pH modifying or buffering agents are well known in the art and can be applied as needed.

The pH of a vehicle of the invention can buffered or unbuffered to a pH of about 3 to about 10. In some embodiments, the pH is buffered to a pH of about 3 to 7. In some embodiments, the pH is buffered to a pH of about 3 to 5. In some embodiments, the pH is buffered to about 4.2. Many orally administered drugs, in liquid or solid form, are stable at stomach pH (typically a pH of about 3 to about 5). By mimicking the natural pH of the stomach without high concentration of acids, a vehicle of the invention can provide a more physiologically correct environment for orally ingested drugs. The moderate sour flavor provided by a pH of about 3 to about 5 has an antagonistic effect with bitter notes, which are commonly rejected notes introduced by medications or preservatives typically incorporated into suspending vehicles. Microbial growth is also suppressed at a pH of about 3 to about 5, allowing us to decrease quantities of preservatives in the vehicle that can impart a bitter taste. A pH in the range of about 3 to about 5 also allows us to use benzoic acid and sorbic acid for preservation in low quantities due to the bactericidal nature of the lower pH and the higher quantity of protonated acid in the vehicle. A vehicle of the invention can also be lightly buffered (10 to 100 mMolar) to keep the osmolality of the vehicle low.

A suspending vehicle of the invention can include natural or artificial sweeteners. The sweetness and/or taste of these artificial sweeteners can be modulated somewhat by the addition of small amounts of nutritive sweeteners. In an embodiment, the amounts of such mono- and di-saccharide nutritive sweeteners such as fructose, high fructose corn syrup and glucose are maintained at low levels to avoid altering the physiological compatibility of the vehicle. Typical natural nutritive sweeteners include, but are not limited to, glucose, high fructose corn syrup, starch hydrolysates, hydrogenated starch hydrolysates, corn syrup solids, sucrose, mannitol, sorbitol, glycerol and other mono- or di-saccharide nutritive sweeteners. The vehicles of the invention generally contain less than 1% w/v, preferably less than 0.1% w/v, more preferably less than 0.075% w/v of such natural sweeteners, but can contain an effective sweetening amount of non-nutritive artificial sweetener. Such sweeteners generally, on a gram by gram basis, have a sweeter character than natural nutritive sweeteners. Typically available sweeteners include, but are not limited to, aspartame (L-asparatryl-L-phenylalanine methyl ester), saccharin (1,2-benzisothiazol-3(2H)-one-1,1-dioxide), stevia, acesulfame K (5,6-dimethyl-1,2,3-oxathiazin-4(3H)-one-2,2 dioxide, potassium salt), sucralose (1,6-Dichloro-1,6-dideoxy-beta-D-fructofuranosyl-4-chloro-4-deoxy-alpha-D-galactopyranoside), and mixtures thereof. Other artificial sweeteners are known. Other known sweeteners that may not be readily available in all countries include, but are not limited to, cyclamate salts, aceslfame, glycyrrhizinate and mixtures thereof. Such a nutritive and non-nutritive sweetening agents can be modified by other compositions to balance sweetness.

The flavor of the liquid vehicle of the invention can be modified to enhance patient acceptance. Commonly available flavorings, aromatic materials, resins and other compositions including both natural and synthetic products can be added to the vehicle. Such materials include, but are not limited to, spearmint flavor, cinnamon flavor, wintergreen flavor, peppermint, eucalyptus, thyme, sage, almond, fruit flavors, and other compatible materials.

The liquid vehicle of the invention can include an acid material that adds a tart or citrus flavor and can aid in the regulation of the osmolality of the substance. Such acids that are typically food grade and physiologically compatible include acids such as lactic, citric, glycolic, maleic, succinic, tannic, acetic, ascorbic, fumeric, phosphoric, tartaric, gluconic and the like. Citric acid, maleic acid, ascorbic acid and other related food grade acids are preferred, either singly or in combination in the liquid vehicles of the invention. Surfactant material can be helpful in blending the liquid vehicle, blending the liquid vehicle with the medicament, and increasing the compatibility of the liquid vehicle with the patient.

Surfactants or surfactant-like molecules can also act as defoaming agents. Such agents include, but are not limited to, anionic surfactants, non-ionic surfactants, amphoteric surfactants and others. Useful surfactants include, for example, sulfonate and sulfate surfactants, polyethylene glycols, polyethylene glycol esters, polyethylene glycol ethers, sorbitan materials known as Span™ and Tween® materials and polyalkylene oxide surfactants also known as pluronic or reverse pluronic surfactants. Siloxane polymers, such as simethicone, are useful for reducing foaming that is likely to occur when the vehicle is shaken or vigorously agitated. These materials are typically added at relatively low amounts and can be used at about 0.001 to about 0.5 grams of the agent per 100 milliliters of the liquid vehicle. These materials also assist in wetting hydrophobic solids added to the vehicle of the invention.

Food grade solvent materials can help increase the compatibility of the liquid vehicle with a medicament and enhance patient compatibility and overall product quality. Such solvents typically include aliphatic alcohols such as methanol and ethanol, dimethylsulfoxide, and others.

The liquid vehicles of the invention may be formulated by adequately combining pharmacologically acceptable carriers or media including, but not limited to, sterilized water, physiological saline, vegetable oil, emulsifiers, suspensions, surfactants, stabilizers, flavoring agents, preservatives, and texture modifiers.

The liquid vehicles of the invention can contain preservative compositions including, but not limited to, benzyl alcohol, parabens, benzoate salts and other well known stabilizing materials. Preservatives that occur naturally in fruits and vegetables can be used in a vehicle of the invention in the same concentration as they occur in nature. In an embodiment, the preservative comprises benzoic acid and sorbic acid. The effectiveness of sorbic and benzoic acids as preservatives can be enhanced by buffering the vehicle to a pH of about 4 to about 5. In another embodiment, the preservative comprises benzoic acid without sorbic acid. In a preferred embodiment, the liquid vehicle contains a minimum quantity of preservative while maintaining product freshness, including antimicrobial and antimycotic effectiveness. In some embodiments, the vehicle of the invention is sterile. In these embodiments, preservatives can be optionally included in the vehicle of the invention.

A general formulation for an embodiment of a liquid vehicle of the invention contains the following:

TABLE 1

| Ingredient | Range (percent by weight) |
| --- | --- |
| Starch | <15% |
| Sweetener | <20% |
| Buffer | <10% |
| Defoaming agent | <4% |
| Preservative | <5% |
| Dye | <3% |
| Flavoring | <5% |
| Water | >70% |

In another embodiment, a vehicle of the invention contains from about 2% to about 6% starch, from about 0.01% to about 1% nutritive or non-nutritive, potent sweetener, 0.1-2.5% buffer, and 0.01 to 1% preservative.

B. Stability

It is impossible to anticipate every possible pharmaceutically active or inactive ingredient that may be compounded into a suspending vehicle of the invention. Many drugs can affect the suspending properties of the preparation adversely. Suspending agents can have sensitivities to a variety of conditions, including, but not limited to, pH of the compounded solution; the ionic strength of the compounded solution; Lewis acidity/basicity of the added ingredients/solution; physical conditions of preparation, including shear and temperature; the presence of metals and/or chelating agents; the presence of soap, soap-like, or detergent type molecules. Powders that settle in finished compounded products are prone to 'packing', where the powder forms a tight cake at the bottom (or top, depending on the density) of the preparation and other problems.

Vehicles of the invention preferably maintain their form and suspending function after chemical or physical perturbation. A vehicle of the invention can tolerate a variety of perturbations including, but not limited to, changes in ionic strength, Lewis acidity/basicity of added ingredients; physical conditions of preparation including shearing, freezing, and heating, the presence of metals and/or chelating agents, and the presence of soap, soap-like, or detergent type molecules.

Powders insoluble in a suspending agent can sediment visibly with time. When a solid is ground before adding it to a suspending vehicle, a distribution of particle sizes occurs. Larger particles will settle more quickly than others in a given vehicle. Ideally, the viscosity of an aqueous suspending vehicle is high enough to sufficiently maintain solids in suspension. However, the vehicle must also be able to be poured easily. For any vehicle, there exists a particle size and density according to Stokes' law that will visibly sediment from the vehicle with time. This leads to inhomogeneous (heterogeneous) preparations of the incorporated drug or inactive ingredients, which, if not vigorously shaken, can result in inaccurate dosing.

Solids that settle in a finished compounded product are prone to packing, where the solids form a tight cake at the bottom or top of the preparation (depending on density). Depending upon how strong this packing is, the product may not be able to be made homogenous (as it was when it was first prepared) by simple shaking of the preparation. A vehicle that prevents sedimented particles from packing tightly is desirable, therefore a homogenous suspension can be reconstituted by simply shaking it.

Embodiments of the invention allow for resuspension of sedimented ingredients. Starch has a unique structure on the 1 to 150 micron scale. When dried, the granules are hard, with little friction between granules, which is the reason it is often used as a glidant in tableting. When the granules are hydrated and/or partially melted, the physical characteristics of the granules change a great deal. The microstructure of hydrated starch granules obtains a very rigid and stable crystallized core with a hydrated outer layer that can resemble a microscopic gel. The gel can vary from a very thin, nearly crystallized core to an extremely soft and sticky exterior outer boundary. While not wishing to be limited by theory, it is believed particles become coated with the sticky starch granules, preventing them from packing tightly with each other. This mechanism is believed to prevent large particles from forming hard cakes in vehicles of the present invention. Preferably, embodiments of the invention allow for easy and quick resuspension of the active ingredient after the initial compounding in the vehicle of the invention. In an embodiment, a drug or inactive ingredient can be suspended or resuspended in a vehicle of the invention without high shear mixing.

C. Physiological Compatibility

Physiologically mismatched compositions can arise from the basic biochemical nature of a vehicle, including osmolality, pH, and sugar (carbohydrate) content. Failure to match the osmolality or pH of a liquid medication to a patient's needs, for example, can result in a medication that is not compatible with a patient. Ingestion of a medication that is hyperosmotic, for example, can result in a quick rejection of the medication by the patient and failure of the treatment.

An important aspect of a vehicle for preparing medicinal suspensions or solutions is osmolality/osmolarity. Osmolarity is the number of solute molecular entities (non-ionizing molecules count as one each, whereas molecules that ionize into n particles when dissolved in water contribute n times their count) per unit volume. Physicians, pharmacists, and nutritionists more frequently refer to osmolality, which is the number of solute molecular entities per unit mass, and is independent of temperature. The use of these terms is roughly interchangeable as the difference in osmolality and osmolarity at temperatures from 0° C. to 100° C. is less than 5% at the limit of infinite dilution, which is about 550 mOsmol.

Blood serum has an osmolality of about 300 mOsmol per kilogram (mOsmol) (Seeley, et. al., *Anatomy & Physiology* 2nd Ed., Allan et al. eds., Mosby-Year Book Inc., St. Louis, Mo., 1992, p. 863). Compounded preparations with high osmolarity (above approximately 300 mOsmol) (http://uthealthinformatics-net/docs/english/ma/hyperosm._ma.asp) are dehydrating when taken orally. When a hyperosmotic preparation is ingested by a patient, water is drawn from the "third space" surrounding the gut (comprised primarily of the small and large bowels) into the lumen of the gut by osmolar pressure until the material in the digestive tract reaches the same osmolality as the surrounding body fluid. This hyperosmotic effect is known as saline laxation and results in some level of dehydration for the patient. Infants, small children, and the elderly are most sensitive to this dehydration. In these sensitive patients, the net flow of water into the lumen of the gut can cause a cycle of diarrhea. As the patient tries to maintain hydration by drinking more water or other hypotonic liquid, bulk laxation can be triggered.

We have surprisingly found that suspending agents comprising a polysaccharide having at least 50% glucose repeating saccharide units and at least 90% alpha linkages are more physiologically compatible to patients than the typical derivatized cellulosic-based suspending agents that are most common in conventional liquid vehicles. Celluloses and derivatized celluloses are non-nutritive, cannot be readily metabolized by the body, and tend to be recognized as foreign materials by the body.

FLAVOR-SWEET™ (HUMCO, Texarkana, Tex.), a sweetening vehicle, and FLAVOR-PLUS™ (HUMCO, Texarkana, Tex.), a suspending vehicle, designed to be mixed in an approximately one-to-one ratio in the final compounded product and ORA-SWEET® (Paddock Laboratories, Minneapolis, Minn.), a sweetening vehicle, and ORA-PLUS® (Paddock Laboratories, Minneapolis, Minn.), which are also designed to be mixed in an approximately 1:1 ratio in the final compounded product, are hyperosmotic (theoretical value of approximately 1700 mOsmol, calculation based on information from the manufacturer's literature) and the cellulosic-based suspending agents can act as a laxative. Another product, Roxane's diluent (flavored) (Roxane Laboratories, Columbus, Ohio), uses PEG-8000 as a viscosity increasing agent. PEG-8000 imparts a bitter flavor note to a medicinal preparation, which is masked in the raw preparation but is likely to form chords with other bitter flavor notes introduced by the incorporation of a variety of drugs. PEG-8000, like the suspending agents in FLAVOR-PLUS and ORA-PLUS for example, has a mild to moderate laxative effect.

Cellulosic suspending agents contain beta linkages between the repeating saccharide units. Beta linkages, unlike alpha linkages, are indigestible by humans. As a result, cellulosic suspending agents can act like bulk laxatives. In contrast, starches are typically linear or branched polysaccharides. The bonds between the carbohydrate monomers in starch can be split readily by biologically active enzymes resulting in mono-, di- and tri-saccharide that are quickly absorbed and metabolized.

The human body is more efficient with the ingestion of hypoosmotic materials (*Remington: The Science and Practice of Pharmacy*, Genarro A. R. ed., $20^{th}$ ed., Lippincott Williams &Wilkins, Philadelphia, Pa., 2000, pp. 744, 321). When a hypoosmotic material is ingested, the flow of water is from the lumen of the gut into the third space providing a net hydrating effect and keeping the gut "dry". Vehicles of the invention can be prepared with very low osmolality. This aspect of the invention enables a compounding pharmacist, for example, to add drugs and/or inactive ingredients in significant concentrations without concern about hypertonicity in the final preparation. In some embodiments, the osmolality of the vehicle of the invention is 300 mOsmol or less, more preferably 200 mOsmol or less, more preferably 100 mOsmol or less, more preferably 50 mOsmol or less, more preferably 20 mOsmol or less. In an embodiment, the osmolality of a vehicle of the invention is from about 30 mOsmol to about 40 mOsmol. In another embodiment, the osmolality of a vehicle of the invention is from about 20 mOsmol to about 30 mOsmol. In some embodiments, the osmolality of a vehicle of the invention is sufficiently low to allow the addition of a drug(s) and inactive ingredients without the osmolality of the final preparation exceeding 300 mOsmol.

In order to obtain physiological compatibility with a patient, we have also carefully controlled the carbohydrate or natural sweetener content in some embodiments of the invention. A vehicle of the invention can be sweetened, for example, with an artificial sweetener and maintain an osmolality of 300 mOsmol or less. The artificial sweetener can be nutritive or non-nutritive. Preferably, the artificial sweetener is a potent sweetener, such as sucralose. A potent artificial sweetener allows for the use of less sweetener, resulting in lower osmolality. In an embodiment, a vehicle of the invention contains less than 1%, preferably less than 0.1% w/v, more preferably less than 0.075% w/v artificial sweetener.

Sweetening a vehicle of the invention with an artificial sweetener can also make the vehicle compatible with a patient having blood glucose sensitivity. For example, patients with diabetes are sensitive to factors that change their blood glucose level. Even patients without diabetes can suffer adverse effects from sudden changes in their blood glucose levels. The blood glucose level is sensitive to the composition of substances taken orally. It is well established that simple sugars and small metabolizeable molecules can cause a spike in the blood glucose level of these individuals. Currently available products rely on natural sugars or reduced sugars for both their texture and sweetness. Reducible sugars can cause blood glucose reactions similar to natural sugars. The ingested medication combined with currently available vehicles containing natural sugars or reduced sugars can drastically alter blood glucose levels, especially in tightly managed patients.

D. Uses

There is often a need to administer solid medications orally in liquid forms to patients. These patients include adults who cannot swallow solid dosage forms, infants or children, non-ambulatory patients with nasogastric tubes, geriatric patients, and animals. Likewise, patients suffering from severe oral traumas or disease could use the vehicles of the invention to ease ingestion of a desired medication. Patients recovering from severe oral trauma, such as mandibular fracture or complex dental procedures, have dysphagia. An embodiment of the invention would ease the transit of the medication from the oral cavity through the pharynx to the esophagus and eventually to the stomach.

The aqueous suspending vehicles of the invention can be combined with a drug, medication, or medicament to form a treatment for a variety of diseases or disorders. Such diseases or disorders include, but are not limited to, cellular hypoproliferation, neoplastic diseases, inflammatory diseases, multiple sclerosis, myocarditis, sinusitis, eczema, periodontal disease, kidney disease and Type 1 diabetes. These diseases are representative; many other diseases or disorders may be treated.

Many drugs or medicaments can be used in the aqueous suspending vehicles of the invention. Starch is known to be a broadly compatible excipient and a binding agent for tablets. The compatibility of starches with many drugs in the presence of water is well established, as many commercial tablets are prepared by wet granulation methods, usually with a starch component. See, for example, U.S. Pat. No. 6,238,695 and http://webusers-xula-edu/tmandal/pharmaceutics/TABLET-ppt). Starch also has a long history in food chemistry, further highlighting its compatibility and stability with the plethora of chemical entities present in all manner of food preparations.

Many liquid or solid drugs and medicaments can be suspended in the vehicle of the invention and administered to a patient. A patient may be a human or an animal. In preferred embodiments, the drug or medicament is a solid or liquid oral dosage form. Some drugs have aqueous intolerance and, as such, should be mixed and administered with little time delay. In some embodiments, the drug is suitable for delivery in an aqueous vehicle. The following are exemplary, non-limiting drugs that can be used in the invention. These drugs include hydrochlorothiazide, cyclosporin, cimetidine, captopril, amoxicillin, acetaminophen, ibuprofen, ranitidine, tetracyclines, vitamin or vitamin supplements, and cephalexin and related compounds. This list is not exhaustive, but contains a number of representative examples. Most drugs in oral dosage form that are useful for treating patients by pharmacists or physicians or other caregivers can be administered using the liquid vehicle of the invention.

In a typical preparation, a drug or medicament available in a tablet or bulk powder form is finely ground, wetted with a wetting agent, and then combined slowly with a liquid vehicle. A vehicle of the invention can be combined with about 0.01 to about 100,000 mg of drug or inactive ingredient per 100 ml of vehicle. The drug or inactive ingredient can be in the form of a liquid, powder, tablet, or capsule. Tablets or capsules are typically ground to a powder before they are combined with the vehicle. In an embodiment, the concentration of the drug is about 1 to about 100 milligrams per 100 ml of the vehicle of the invention. This technique is flexible and provides a method to treat a patient with a variety of medicaments in an alternative dosage form.

EXAMPLES

The present invention may be better understood with reference to the following examples. These examples are intended to be representative of specific embodiments of the invention and are not intended as limiting the scope of the invention.

In some of the examples, an embodiment of the invention containing a starch suspending agent is evaluated in side-by-side testing with a 1:1 mixture of ORA-SWEET SF® and ORA-PLUS® (Paddock Laboratories, Minneapolis, Minn.). ORA-SWEET SF® is an example of a sweetening vehicle and contains the nutritive sweetener sorbitol. ORA-PLUS® is an example of a suspending vehicle and contains the α-glycan cellulosic suspending agents microcrystalline cellulose, sodium carobxymethylcellulose, and xanthan gum. ORA-SWEET SF® and ORA-PLUS® are designed to be mixed in an approximately 1:1 ratio in the final compounded product. The 1:1 mixture of ORA-SWEET SFS® and ORA-PLUS® was prepared in all examples according to the manufacturer's directions. The 1:1 mixture of ORA-SWEET SF® and ORA-PLUS® is hereinafter referred to as "OO" in the examples.

Example 1

An embodiment of the liquid vehicle of the invention contains the following ingredients:

TABLE 2

| Ingredient | Quantity (g) | (w/w % relative to water) |
| --- | --- | --- |
| PURE-GEL ® 994 | 884.9 | 4.25 |
| Sucralose | 15.615 | 0.075 |
| Simethicone | 0.2082 | 0.001 |
| Sodium Benzoate | 12.43 | 0.060 |
| Citric Acid | 8.09 | 0.039 |
| Distilled Water | 20820 | |

The embodiment shown in Table 2 (available commercially as SYRSPEND™ SF (Gallipot, St. Paul, Minn.)) was prepared with standard amylase prevention measures. To produce the above embodiment, the starch suspending agent PURE-GEL® 994(884.9 g; Grain Processing Corp., Muscatine, Iowa), simethicone (0.2082 g), sodium benzoate (12.43 g), and 75% of the distilled water (15615 g) were combined in a single vessel and heated to between 95° C. and 100° C. with constant stirring for 30 minutes. The heated mixture was cooled with continuous stirring to at least 40° C. and then cool water was added to bring the volume of the cooled mixture to the pre-heating volume. The citric acid (8.09 g) and sucralose (15.615 g) was dissolved in sufficient water to complete solubilization. This solution was added with stirring to the cooled mixture, along with the remaining distilled water. The batch size of the liquid vehicle was 20820 g (in grams water).

The process produced a cloudy liquid with a syrupy texture that had a total theoretical osmolality of 23.3 mOsmol. The osmolality of the liquid vehicle shown in Table 2 was determined experimentally by Advanced Instruments, Inc. (Norwood, Mass.) with a model 3D2 quality control osmometer and a model 210 Osmometer (Advanced Instruments, Norwood, Mass.). The model 3D2 osmometer was calibrated with five 100 mOsm/kg $H_2O$ and five 900 mOsm/kg $H_2O$ laboratory standards (Advanced Instruments, Norwood, Mass.) and then the osmolality of ten 250 µl samples of the liquid vehicle was measured with the calibrated osmometer. The model 210 osmometer was calibrated with three 50 mOsm/kg $H_2O$ and three 850 mOsm/kg $H_2O$ laboratory standards (Advanced Instruments, Norwood, Mass.) and then the osmolality of ten 20 µl samples of the liquid vehicle was measured with the calibrated osmometer. The liquid vehicle had experimental osmolality of 36 to 39 mOsmol (data not shown).

Example 2

An embodiment of the liquid vehicle of invention contains the following ingredients:

TABLE 3

| Ingredient | Quantity (g) | | (w/w % relative to water) |
| --- | --- | --- | --- |
| PURE-GEL ® 994 | | 936.9 | 4.5 |
| Sucralose | | 15.615 | 0.075 |
| Simethicone | | 0.2082 | 0.001 |
| Benzoic Acid | | 10.2902 | 0.049 |
| Sodium Benzoate | | 12.4251 | 0.060 |
| Buffer | Quantity (g) | 44.0031 | 0.211 |
| Malic Acid | 7.6372 | | |
| Citric Acid | 11.5714 | | |
| Sodium Citrate | 24.7945 | | |
| Total | 44.0031 | | |
| Distilled Water | | 20820 | |

The embodiment shown in Table 3 was prepared with standard amylase prevention measures. To produce the above embodiment, the starch suspending agent PURE-GEL® 994 (936.9 g; Grain Processing Corporation, Muscatine, Iowa), simethicone (0.2082 g), benzoic acid (10.2902 g), sodium benzoate (12.4251 G), and 75% of the distilled water (15615 g) were combined in a single vessel and heated to between 95° C. and 100° C. with constant stirring for 30 minutes. The heated mixture was cooled with continuous stirring to at least 40° C. and then cool water was added to bring the volume of the cooled mixture to the pre-heating volume. The buffer and sucralose (15.615 g) was dissolved in sufficient water to complete solubilization. This solution was added with stirring to the cooled mixture, along with the remaining distilled water. The buffer was a batch mixture of malic acid, citric acid, and sodium citrate in the proportions described in Table 3. The batch size of the liquid vehicle was 20820 g (in grams water). The process produced a cloudy liquid with a syrupy texture that had a total theoretical osmolality of 37.0 mOsmol.

Example 3

An embodiment of the liquid vehicle of the invention contains the following ingredients:

TABLE 4

| Ingredient | Quantity (g) | | (w/w % relative to water) |
| --- | --- | --- | --- |
| INSCOSITY ™ 658 | | 1135.6 | 5.0 |
| Sucralose | | 17.03 | 0.075 |
| Simethicone | | 0.227 | 0.001 |
| STABILITE ™ SD30 | | 2271 | 10.0 |
| Benzoic Acid | | 8.59 | 0.1 (total benzoate) |
| Sodium Benzoate | | 14.12 | 0.1 (total benzoate) |
| Sorbic Acid | | 22.71 | 0.1 |
| Buffer | Quantity (g) | 48.00 | 0.211 |
| Malic Acid | 7.613 | | |
| Ascorbic Acid | 10.000 | | |
| Citric Acid | 5.672 | | |
| Sodium Citrate | 24.714 | | |
| Total | 48.00 | | |
| Distilled Water | | 22712 | |

The embodiment shown in Table 4 was prepared with standard amylase prevention measures. To produce the above embodiment, the starch suspending agent INSCOSITY™ 658 (1135.6 g; Grain Processing Corp., Muscatine, Iowa), simethicone (0.227 g), the sorbic acid (22.71 g), the benzoic acid (8.59 g), the sodium benzoate (14.12 g), and 75% of the distilled water (17034 g) were combined into a single vessel and heated to between 80° C. and 85° C. with constant stirring for 5 minutes. The heated mixture was cooled with continuous stirring to at least 40° C. Sucralose (17.03 g), STABILITE™ SD30 (2271 g; SPI Polyols, New Castle, Del.), and the buffer (48 g) were dissolved in sufficient water to complete solubilization. This solution was added with stirring to the cooled mixture, along with the remaining distilled water. The buffer was a batch mixture of malic acid, ascorbic acid, citric acid, and sodium citrate in the proportions described in Table 4. The batch size of the liquid vehicle was 22712 g (in grams water).

The process produced a liquid with a syrupy and sticky texture that had a theoretical osmolality of 185 mOsmol. The above embodiment can be produced without heating as the INSCOSITY™ starch is pre-hydrated. In such an embodiment, the first mixing step is carried out at room temperature (20° C. to 25° C.) with constant stirring until the sorbic acid and benzoic acid are completely dissolved. Heat was applied in the process described above to simply speed the dissolution of the sorbic acid and benzoic acid.

Example 4

Chemical Perturbations do not Thin a Vehicle Containing a Starch Suspending Agent A vehicle for preparing a medicinal suspension should maintain its form and function after perturbation by a variety of factors. Conditions that affect the form and function of a suspending vehicle include, but are not limited to, ionic strength, Lewis acidity/basicity, and freezing and heating. We assessed the impact of these chemical perturbations on the viscosity of a vehicle containing a starch suspending agent (vehicle of Example 1 (VE1) and a vehicle containing microcrystalline cellulose and carboxymethycellulose suspending agents (OO). This example demonstrates that a vehicle containing a starch suspending agent is less sensitive to freezing/heating perturbations than a vehicle containing microcrystalline cellulose and carboxymethycellulose suspending agents.

Methods

The viscosity of OO or the vehicle of Example 1 was measured before and after the addition of potassium bromide, aluminum chloride, or EDTA disodium salt. The viscosity was measured with Brookfield RVDV-III Ultra rheometer from Brookfield Engineering Laboratories, Inc., Middleboro, Mass., using the small sample adapter with spindle SC4-21 at 100 RPM. The potassium chloride (0.36 g) aluminum chloride (0.40 g), or EDTA disodium salt (1.12 g) was added to 10 ml of OO or the vehicle of Example 1 and the vehicle was shaken for 5 minutes. The vehicle was allowed to stand for 30 minutes and then the viscosity of the vehicle was measured.

The viscosity of OO or SS was also measured before and after a freeze-heat cycle using Brookfield RVDV-III Ultra rheometer with a SC4-21 spindle/small sample adapter at 100 RPM (Brookfield Engineering Laboratories, Inc., Middleboro, Mass.). All measurements were carried out at 22° C.±2° C. Ten ml of OO or SS was frozen, heated in a water bath to 80° C., refrozen, heated in a water bath to 80° C., and then allowed to cool to 22° C.±2° C. The viscosity of the vehicle was measured once the vehicle cooled to 22° C.±2° C.

Results

The results of the experiment are shown in Table 5. The vehicle containing microcrystalline cellulose and carboxymethycellulose suspending agents (OO) was sensitive to the freeze-heat perturbation, whereas the vehicle containing a starch suspending agent (VE1) was not. OO thinned significantly (approximately 10%) percent after the freeze-heat cycle. In contrast, the VE1 thickened slightly after the freeze-heat cycle. The ionic strength, Lewis acid, and Lewis base perturbations did not significantly affect the viscosity of OO. The Lewis base perturbation did not significantly affect the viscosity of VE1. VE1 thickened slightly after ionic strength perturbation and thinned slightly after Lewis acid perturbation. This loss of viscosity is minor as the viscosity of VE1 is sufficiently high, as shown in Example 5, to maintain particles in suspension.

TABLE 5

| Vehicle | Probed Perturbation | Chemical | g/10 mL vehicle | Starting Viscosity | Final Viscosity |
|---|---|---|---|---|---|
| OO | Ionic Strength | Potassium Bromide | 0.36 | 54.0 | 54.5 |
| VE1 | Ionic Strength | Potassium Bromide | 0.36 | 184.5 | 207.0 |
| OO | Lewis Acid | Aluminum Chloride | 0.40 | 54.0 | 53.0 |
| VE1 | Lewis Acid | Aluminum Chloride | 0.40 | 184.5 | 173.0 |
| OO | Lewis Base | EDTA, disodium salt | 1.12 | 54.0 | 53.5 |
| VE1 | Lewis Base | EDTA, disodium salt | 1.12 | 184.5 | 182.0 |
| OO | Freeze-Heat | Freeze, Heat in Water bath, cool to 22° C. ± 2° C. (2x) | N/A | 54.0 | 50.5 |
| VE1 | Freeze-Heat | Freeze, Heat in Water bath, cool to 22° C. ± 2° C. (2x). | N/A | 184.5 | 237.0 |

Example 5

Suspendability of Drugs in a Vehicle Containing a Starch Suspending Agent

Suspendability of insoluble ingredients and resuspendability of insoluble ingredients that have sedimented are important characteristics for a compounding vehicle. Insoluble pharmaceutically active or inactive ingredients in a suspending vehicle can sediment with time. Sedimentation of these ingredients results in heterogeneous preparations of the incorporated active or inactive pharmaceutical ingredients, which if not vigorously shaken, can result in inaccurate dosing. The risk of inaccurate dosing is reduced the longer a vehicle can maintain insoluble pharmaceutical ingredients in suspension.

The suspendability of five different drugs was evaluated in a vehicle containing a starch suspending agent (vehicle of Example 1 (VE1)) and a vehicle containing microcrystalline cellulose and carboxymethycellulose suspending agents (OO). This example demonstrates that a vehicle containing a starch suspending agent maintained each of the five drugs in suspension for 7 days with minimal sedimentation. In contrast, two of the five drugs settled significantly in the vehicle containing microcrystalline cellulose and carboxymethycellulose suspending agents.

Methods

Suspensions of baclofen, bethanechol chloride, labetalol hydrochloride, verapamil hydrochloride, or ibuprofen were prepared in VE1 or OO. Commercially available tablets were ground in a tablet grinder (Gallipot, Inc., St. Paul, Minn.; Item#101132) to a fine powder and wetted with a minimal quantity of propylene glycol. The wetted powder was incorporated into 50 ml VE1 or OO by geometric dilution and stored in individual non-opaque containers. Table 6 shows the number of tablets added to VE1 or OO and the concentration of drug per ml of VE1 or OO. The concentrations of the pharmaceutical compounds in suspension represent 'typical' prescribed preparations.

TABLE 6

| Drug Name | Number of Tablets/50 ml | Concentration of Drug (mg/mL) |
|---|---|---|
| Baclofen | 50 | 10 |
| Bethanechol Chloride | 5 | 5 |
| Labetalol Hydrochloride | 7 | 42 |
| Verapamil Hydrochloride | 31¼ | 50 |
| Ibuprofen | 1¼ | 20 |

The suspensions were evaluated immediately after preparation with respect to ease of preparation, homogeneity, and viscosity by the pharmaceutical technician preparing the suspensions. The suspensions were rated on a subjective scale of 0-10: ease of preparation, 0=difficult, 10=very easy; homogeneity, 0=drug settles completely and immediately, 10=consistently homogenous in appearance along the vertical axis; viscosity, 0=water, 10=thick molasses.

The suspensions were stored in the dark at room temperature for 7 days and then settling of the drugs and resuspendability of sedimented drug in OO or VE1 was evaluated. Settling and resuspendability of the drugs was rated on a subjective scale of 0-10: settling (how much product apparent at bottom of container, 10=none, 0=all); resuspendability (how homogenous does the product appear after moderate shaking, 10=perfectly homogenous, 0=not homogenous (heterogeneous)). Resuspendability of sedimented ingredients was evaluated after evaluation of settling. The suspensions were shaken deliberately (stepwise), with frequent inspections of the bottom of the container.

Results

The results for ease of preparation, homogeneity, and viscosity are summarized in Table 7.

TABLE 7

| | Ease of Preparation | | Homogeneity | | Viscosity | |
|---|---|---|---|---|---|---|
| Drug | VE1 | OO | VE1 | OO | VE1 | OO |
| Baclofen | 10 | 9 | 9 | 9 | 7 | 6 |
| Ibuprofen | 10 | 10 | 9 | 9 | 7 | 4 |
| Labetalol Hydrochloride | 8 | 1 | 9 | 3 | 7 | 1 |
| Bethanechol Chloride | 10 | 10 | 9 | 9 | 7 | 5 |
| Verapamil Hydrochloride | 10 | 3 | 9 | 8 | 7 | 2 |

VE1 preparations were generally rated as easier to prepare than the OO preparations by a pharmaceutical technician (average 9.6, 0.89 standard deviation (SD) vs. average 6.6, 4.28 SD) VE1 preparations were consistent with respect to homogeneity of the prepared suspensions (average 9, 0.0 SD). The opaque nature of VE1, however, may have masked some of the heterogeneity in the distribution of the drug. OO preparations demonstrated greater variability in homogeneity (average 7.6, 2.61 SD). In preparations of labetol hydrochloride and verapamil hydrochloride in OO, there appeared to be a phase separation of the suspending agent from the liquid phase. The viscosities of the VE1 preparations were consistent (average 7, 0.0 SD). The viscosity of control VE1 (VE1 prior to the addition of any of the drugs) was evaluated as 7. The viscosity of the OO preparations was variable (average 3.6, 2.07 SD). The viscosity of control OO (OO prior to the addition of any of the drugs) was evaluated as 6. Much of the variability in the viscosity of the OO preparations can be attributed to the phase separation observed in the labetol hydrochloride and verapamil hydrochloride preparations. In the OO preparations in which phase separation was observed, a sharp decrease in viscosity relative to the control OO was apparent.

The results for settling and resuspendability of sedimented ingredients are summarized in Table 8.

TABLE 8

| | Settling | | Resuspendability | |
|---|---|---|---|---|
| Drug | VE1 | OO | VE1 | OO |
| Baclofen | 8 | 6 | 9 | 9 |
| Ibuprofen | 8 | 7 | 9 | 9 |
| Labetalol Hydrochloride | 9 | 2 | 9 | 3 |
| Bethanechol Chloride | 8 | 6 | 9 | 9 |
| Verapamil Hydrochloride | 7 | 2 | 9 | 6 |

The vehicle containing a starch suspending agent (VE1) maintained each of the five drugs in suspension for 7 days with minimal sedimentation. The drugs easily were resuspended in VE1 after settling. The vehicle containing microcrystalline cellulose and carboxymethycellulose suspending agents (OO) maintained three of the five drugs in suspension for 7 days. Baclofen, ibuprofen, and bethanechol chloride were suspended in OO after 7 days with minimal to moderate sedimentation. A large portion of the labetalol hydrochloride and verapamil hydrochloride had settled in the OO after 7 days. Baclofen, ibuprofen, and bethanechol chloride were easily resuspended in OO after settling. Labetalol hydrochloride and verapamil hydrochloride were more difficult to resuspend in OO after settling.

Example 6

Resuspendability of Calcium Carbonate in a Vehicle Containing a Starch Suspending Agent Some pharmaceutically active or inactive ingredients can form cakes at the bottom or top of a liquid vehicle (depending on density) that are difficult to resuspend with shaking. Calcium carbonate (precipitated, heavy) is a particularly challenging compound to resuspend in a liquid vehicle. Calcium carbonate is dense and hydrophilic, therefore it minimally interacts with suspending agents and forms cakes in many suspending vehicles that are difficult to resuspend. The particle size distribution of calcium carbonate is also larger than many drug preparations.

The resuspendability of calcium carbonate in a vehicle containing a starch suspending agent (vehicle of Example 1 (VE1)) and a vehicle containing microcrystalline cellulose and carboxymethycellulose suspending agents (OO) was evaluated. This example demonstrates that calcium carbonate is more easily resuspended in a vehicle containing a starch suspending agent than in a vehicle containing microcrystalline cellulose and carboxymethycellulose suspending agents.

Methods

Five ml of VE1 or OO was added to a 12×75 mm test tube. Five hundred mg of calcium carbonate (precipitated, heavy) was added to each tube and the tubes were vigorously shaken for three minutes at room temperature. The test tubes were then covered, set upright in a beaker, and allowed to stand undisturbed for 16 hours at room temperature. The test tubes were then gently inverted and reoriented to an upright position five times. After the fifth inversion cycle, the test tubes were subjected to vigorous shaking, one shake at a time. The size of the cake in the test tubes was observed after each inversion cycle or shake and recorded. The size of the cake was rated on a qualitative scale from 0 to 10, with 0 representing no observable cake and 10 representing the quantity of cake observed in the OO preparation before the first inversion cycle.

Results

The results of the experiment are shown in Table 9. Calcium carbonate was more easily resuspended in a vehicle containing a starch suspending agent (VE1) than a vehicle containing microcrystalline cellulose and carboxymethycellulose suspending agents (OO). When the calcium carbonate was first added to the vehicle samples, OO did not wet the calcium carbonate as easily or as quickly as the vehicle of Example 1. This observation was not unexpected as OO has a higher osmolality than the vehicle of Example 1.

TABLE 9

| Repetition # | VE1 | OO |
| --- | --- | --- |
| Inversion 1 | 8 | 10 |
| Inversion 2 | 6 | 9 |
| Inversion 3 | 5 | 8 |
| Inversion 4 | 3 | 7 |
| Inversion 5 | 2 | 7 |
| Shake 1 | 1 | 5 |
| Shake 2 | 1 | 5 |
| Shake 3 | 1 | 4 |
| Shake 4 | 0 | 3 |
| Shake 5 | 0 | 3 |
| Shake 6 | 0 | 2 |
| Shake 7 | 0 | 1 |
| Shake 8 | 0 | 0 |

Example 7

Rheology of a Vehicle Containing a Starch Suspending Agent

The rheology of a liquid vehicle is important to both the suspending and handling properties of the vehicle. A liquid suspending vehicle ideally is a pseudoplastic power law fluid with a low flow index or has a measurable yield value (Thompson, J. E., Davidow L. *A Practical Guide to Contemporary Pharmacy Practice*, 2nd ed., Lippincott Williams & Wilkins, Baltimore, Md., 2004, p. 28.1-28.23). Power law fluids with flow indexes less than 1 are pseudoplastic. The closer the flow index is to zero, the greater the viscosity at low shear rates. At the shear rates generated by sedimentation, the flow index of a suspending vehicle ideally decreases as the shear rate decreases. Another important rheological characteristic of a liquid vehicle is thixotropy. A liquid suspending vehicle ideally is thixotropic, meaning the viscosity of the vehicle increases as the vehicle sits undisturbed (Thompson, J. E., Davidow L. *A Practical Guide to Contemporary Pharmacy Practice*, $2^{nd}$ ed., Lippincott Williams & Wilkins, Baltimore, Md., 2004, p. 28.1-28.23).

The rheology of a vehicle containing a starch suspending agent (vehicle of Example 1 (VE1)) and a vehicle containing microcrystalline cellulose and carboxymethycellulose suspending agents (OO) was compared. This example demonstrates that the vehicle containing a starch suspending agent is thixotropic and has higher viscosity than the vehicle containing microcrystalline cellulose and carboxymethycellulose suspending agents at shear rates generated by sedimentation.

Methods

All rheology measurements were carried out with a Brookfield RVDV-III Ultra rheometer (Brookfield Engineering Laboratories, Inc., Middleboro, Mass.). Viscosity and shear stress and shear rate measurements were analyzed with Rheocalc32 software, version 2.6.0.32 (Brookfield Engineering Laboratories, Inc., Middleboro, Mass.). Static yield value measurements were analyzed with EZ-Yield software, version 1.0.2.17 (Brookfield Engineering Laboratories, Inc., Middleboro, Mass.). Viscosity, shear stress, and shear rate measurements were obtained using a small sample adapter with spindle SC4-21 (Brookfield Engineering Laboratories, Inc., Middleboro, Mass.). Static yield value measurements were obtained using vane spindles, which are identified by their number in the specific experiments. All measurements were carried out at 22° C.±2° C.

As the RPM of the instrument is the independent variable for the experiments, its exact value is specified with each experiment. Note that while the RPM is the controlled parameter, we report shear rate as the independent variable, since it is the physical quantity being controlled (and is directly related to RPM), and is not dependent on the particular instrument.

Results

Figure 2:
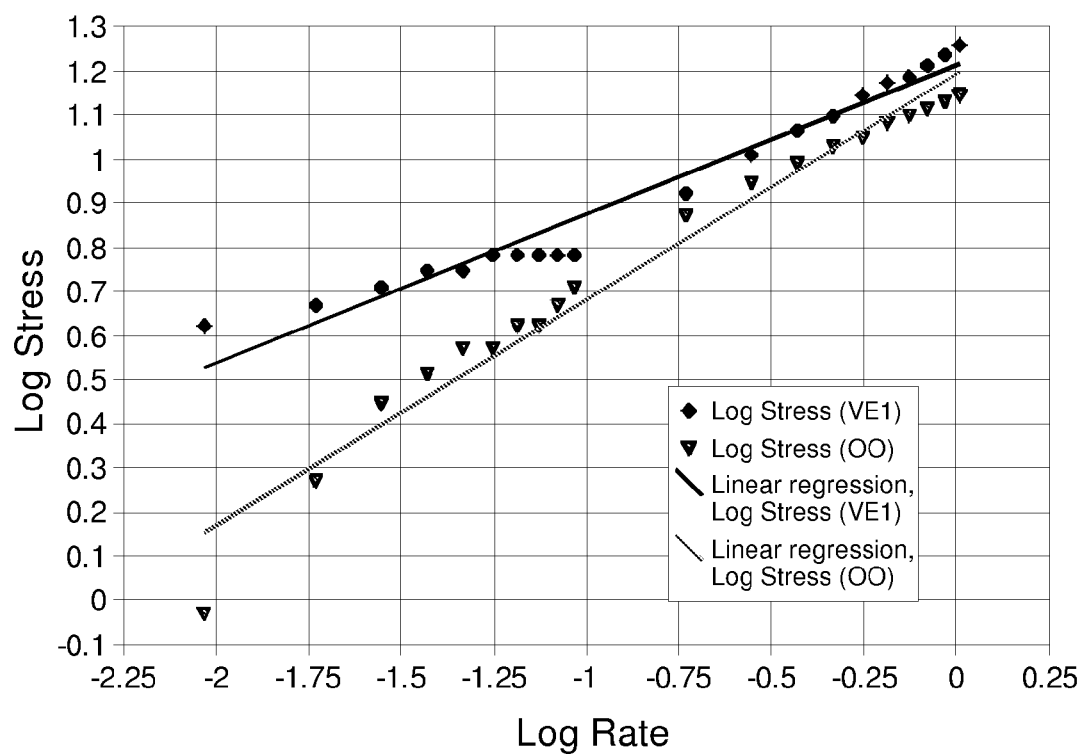
FIG. 2 shows shear stress of an embodiment of the invention (VE1) and a 1:1 mixture of ORA-SWEET SF® and ORA-PLUS® (OO) at shear rates from 0.01 to 1.

FIG. 1 shows a scan of shear rates ranging from 0.1 to 100, with the log of the shear rates being evenly spaced to minimize sampling error for the power law modeling. In this experiment, the RPMs were varied from 0.1 to 100 RPMs, with data points chosen such that the log of the shear rates gave 30 equally spaced values. The vehicle containing a starch suspending agent (VE1) and the vehicle containing microcrystalline cellulose and carboxymethycellulose suspending agents (OO) were held at the indicated shear rate long enough to provide a stable reading on the instrument. Deviations from the linear fit lines are indications of the fluids having non-ideal power law behavior. VE1 had an upward curve at low shear rates indicating that the flow index is decreasing as the shear rate increases. In contrast, OO had a downward curve indicating that the flow index is increasing as the shear rate increases FIG. 2 shows a scan of shear rates ranging from 0.1 to 1, which is near the limit of the rheometer. In this experiment, the RPMs were varied from 0.01 to 1, in 20 evenly spaced values. The vehicle containing a starch suspending agent (VE1) and the vehicle containing microcrystalline cellulose and carboxymethycellulose suspending agents (OO) were held at the indicated shear rate long enough to provide a stable reading on the instrument. VE1 had an upward curve at low shear rates, indicating that the flow index is decreasing as the shear rate increases. In contrast, OO had a downward curve indicating that the flow index is increasing as the shear rate increases.

FIGS. 1 and 2 demonstrate that the vehicle containing a starch suspending agent (VE1) has a higher viscosity at all measured shear rates than the vehicle containing microcrystalline cellulose and carboxymethycellulose suspending agents (OO) and that the flow index of VE1, in contrast to OO, decreases as the shear rate approaches low values. At the shear rates generated by sedimentation, the viscosity of VE1 is significantly higher than OO yet the material maintains workability and ease of handling for pharmaceutical compounding as the handling takes place at much higher shear rates.

Figure 3:
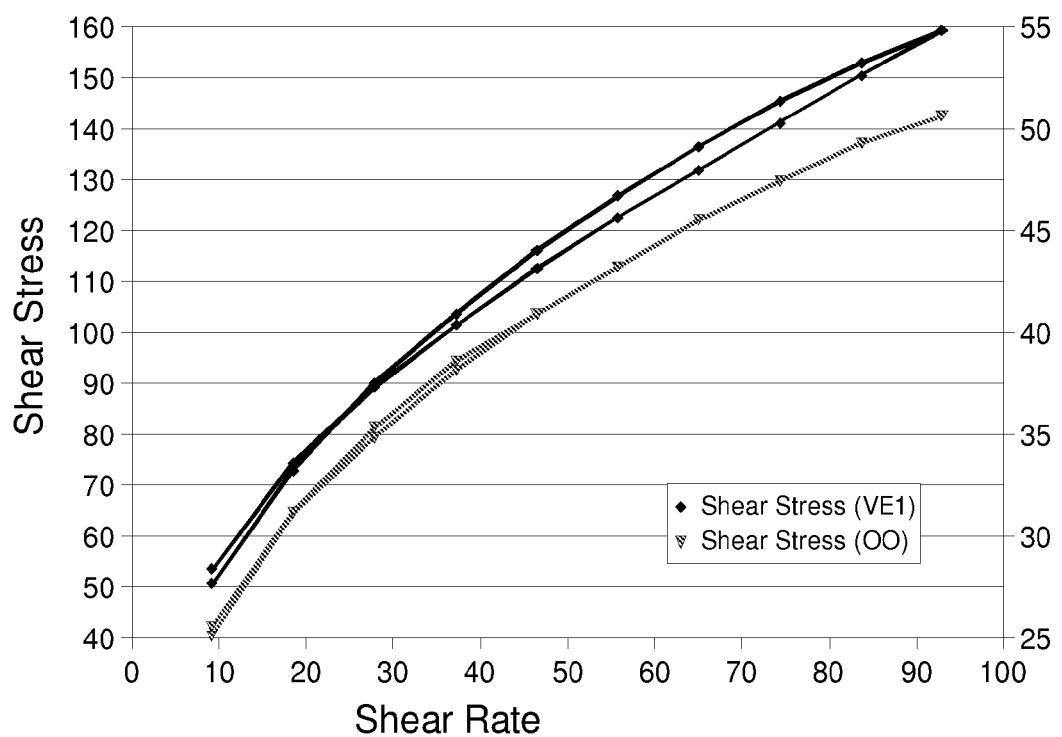
FIG. 3 shows shear stress of an embodiment of the invention (VE1) and a 1:1 mixture of ORA-SWEET SF® and ORA-PLUS® (OO) as shear rate is steadily increased and then decreased. The shear stress of VE1 is plotted against the left y-axis and the shear stress of OO is plotted against the right y-axis.

FIG. 3 shows the results of a rate scan experiment, where the shear stress is measured as the shear rate is steadily increased from its original value and then decreased to its original value. In this experiment, the shear stress was measured at 10, 20, 30, 40, 50, 60, 70, 80, 90, 100, 90, 80, 70, 60, 50, 40, 30, 20, 10 RPMs, with five seconds at each speed to ensure a stable reading on the instrument. In this experimental system, thixotropic fluids display hysteresis due to the shear history of the sample. In FIG. 3, the shear stress of the vehicle containing a starch suspending agent (VE1) is plotted against the left y-axis and the shear stress of the vehicle containing microcrystalline cellulose and carboxymethycellulose suspending agents (OO) is plotted against the right y-axis. In contrast to VE1, OO lacks hysteresis. The data indicates that VE1, but not OO, is thixotropic.

Figure 4:
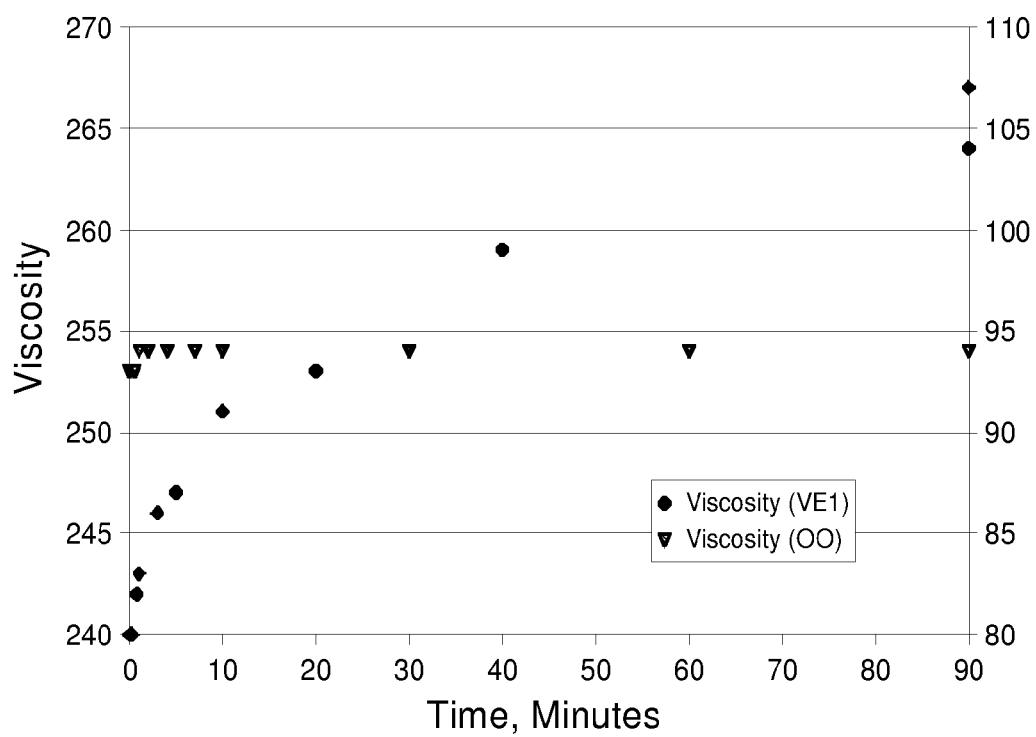
FIG. 4 shows the viscosity of an embodiment of the invention (VE1) and a 1:1 mixture of ORA-SWEET SF® and ORA-PLUS® (OO) over time.

FIG. 4 shows a thixotropy experiment in which VE1 and OO were allowed to remain undisturbed for varying lengths of time. In this experiment, the VE1 and OO were pre-sheared for 5 minutes at 100 RPM. The spindle was then stopped, and 15 seconds elapsed before restarting the spindle speed to 100 RPM. Shear stress was continuously monitored. After 20 seconds of measurement at 100 RPM, the spindle was stopped, and another time period elapsed before repeating the above measuring protocol. At each 'wait period', the maximum shear stress was taken as the value for that wait period. This does not provide a true measurement of thixotropy as the act of measuring the shear stress requires the sample be stressed, which disturbs the sample. Regardless, FIG. 4 demonstrates that vehicle containing a starch suspending agent (VE1) thickens with time, whereas the vehicle containing microcrystalline cellulose and carboxymethycellulose suspending agents (OO) does not.

Example 8

An embodiment of the liquid vehicle of the invention contains the following ingredients:

TABLE 10

| Ingredient | Quantity (g) | (w/w % relative to water) |
|---|---|---|
| STA-Rx | 1457.4 | 7.0 |
| Sucralose | 20.82 | 0.1 |
| Simethicone | 0.2082 | 0.001 |
| Benzoic Acid | 12.43 | 0.060 |
| Distilled Water | 20820 | |

The embodiment shown in Table 10 was prepared with standard amylase prevention measures. To produce the above embodiment, the starch suspending agent STA-Rx (Tate & Lyle/A. E. Staley, Decatur, Ill.) (1457.4 g), simethicone (0.2082 g), benzoic acid (12.43 G), and 75% of the distilled water (15615 g) were combined in a single vessel and heated to between 95° C. and 100° C. with constant stirring for 30 minutes. The heated mixture was cooled with continuous stirring to at least 40° C. and then cool water was added to bring the volume of the cooled mixture to the pre-heating volume. The sucralose (20.82 g) was dissolved in sufficient water to complete solubilization. This solution was added with stirring to the cooled mixture, along with the remaining distilled water. The batch size of the liquid vehicle was 20820 g (in grams water). The process produced a viscous, semisolid liquid with a total theoretical osmolality of 15 mOsmol.

The rheology of the embodiment shown in Table 10 was analyzed as described in Example 7. The liquid vehicle was a power law fluid and had a flow index of 0.26 and a consistency index of 18,617 centipoise (Brookfield RVDV-III Ultra, using spindle SC4-21, and measuring viscosities from 0.1 to 10 RPM). The liquid had a static yield value of 463 dynes/cm$^2$ (Brookfield RVDV-III Ultra, 0.01 RPM, Vane 73, 20 second 6 RPM pre-shear interval with 30 second wait time after auto-zeroing at 0.5 RPM). The yield value of the liquid vehicle is theoretically sufficient to suspend 0.5 mm cubes of silver indefinitely. The liquid vehicle was shear thinning (pseudoplastic) and could be poured with a small amount of agitation (viscosity of about 3700 centipoise at a shear rate of 9.3 sec$^{-1}$). The thixotropy of this embodiment was not measured, as the yield value was sufficient to give permanent suspensions.

Example 9

An embodiment of the liquid vehicle of the invention contains the following ingredients:

TABLE 11

| Ingredient | Quantity (g) | (w/w % relative to water) |
|---|---|---|
| Pure Gel 994 | 295 | 3.900 |
| Sucralose | 5.68 | 0.075 |
| Simethicone | 0.0757 | 0.001 |
| Calcium Carbonate (Light precipitated, powder) | 379 | 5.000 |
| Water | 7571 | |

The embodiment shown in Table 11 was prepared with standard amylase prevention measures. To produce the above embodiment, the starch suspending agent PURE-GEL® 994 (295 g), simethicone (0.0757 g), and 75% of the distilled water (5678.25 g) were combined in a single vessel and heated to between 95° C. and 100° C. with constant stirring for 30 minutes. The heated mixture was cooled with continuous stirring to at least 40° C. and then cool water was added to bring the volume of the cooled mixture to the pre-heating volume. The sucralose (15.615 g) was dissolved in sufficient water to complete solubilization. This solution was added with stirring to the cooled mixture, along with the remaining distilled water. The batch size of the liquid vehicle was 7571 g (in grams water). The process produced a liquid with a syrupy texture that had a total theoretical osmolality of 2.5 mOsmol. The pH of the vehicle is approximately 9.8. The calcium carbonate is very sparingly soluble at pH 9.8 (about 0.00012 mol/L) but becomes more soluble (and more active as a base) as the pH decreases (About 0.01 mol/L at pH 7).

The rheology of the embodiment shown in Table 11 was analyzed as described in Example 7. The liquid vehicle was a power law fluid having a flow index of 0.76, and a consistency index of 656 centipoise (Brookfield RVDV-III Ultra, using spindle SC4-21, and measuring viscosities from 0.1 to 10 RPM, corrected for dynamic yield value of 73.7 dynes/cm$^2$). The vehicle had a static yield value of 107 dynes/cm$^2$, which is theoretically capable of suspending 0.1 mm silver cubes indefinitely (Brookfield RVDV-III Ultra, 0.1 RPM, Vane 72, 20 second 6 RPM pre-shear interval with 30 second wait time after auto-zeroing at 0.5 RPM). The thixotropy of this embodiment was not measured, since the yield value is sufficient to give permanent suspensions.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. A method of preparing a drug in an oral dosage form for treatment of a patient, comprising admixing the drug with a vehicle to form an oral dosage form wherein the drug is suspended in the vehicle, the vehicle comprising:
    a) an aqueous medium;
    b) about 1% to about 15% by weight of a suspending agent, wherein the suspending agent is a starch or glycogen;
    c) an artificial sweetener;
    d) a pH of about 3 to about 10;
    e) a buffer comprising an organic acid, inorganic acid, salts thereof, or mixtures thereof; and
    f) osmolality of about 300 mOsmol or less;
    wherein the vehicle is thixotropic and a pseudoplastic power law fluid comprising a consistency index of at least 400 at a shear rate of about 1 $sec^{-1}$.

2. The method of claim 1, wherein the starch is a modified starch.

3. The method of claim 1, wherein the starch comprises an amylose to amylopectin ratio of about 20%:80% to about 60%:40% by weight.

4. The method of claim 1, wherein the vehicle comprises a yield value greater than 0.

5. The method claim 4, wherein the vehicle comprises a yield value of about 0.01 $dynes/cm^2$ to about 60 $dynes/cm^2$.

6. The method of claim 4, wherein the vehicle comprises a flow index of less than about 0.8 at a shear rate of less than about 1 $sec^{-1}$.

7. The method of claim 1, wherein the vehicle comprises a pH of about 3 to about 5.

8. The method of claim 1, wherein the vehicle further comprises:
    a) a preservative;
    b) an antimicrobial agent;
    c) an anti-oxidant;
    d) a flavoring agent;
    e) a flavor enhancer;
    f) a colorant;
    g) a texture modifier;
    h) a surfactant; or
    i) a defoaming agent.

9. The method of claim 1, wherein the organic acid comprises malic acid, citric acid, ascorbic acid, tartaric acid, adipic acid, lactic acid, fumaric acid, maleic acid, acetic acid, phosphoric acid, a salt thereof, or mixtures thereof.

10. The method of claim 1, wherein the artificial sweetener comprises sucralose, aspartame, saccharin, stevia, acesulfame-K, or mixtures thereof.

11. The method of claim 1, wherein the vehicle comprises about 1% or less artificial sweetener by weight.

12. The method of claim 1, wherein the vehicle comprises osmolality of about 50 mOsmol or less.

13. The method of claim 1, wherein the vehicle comprises osmolality of about 30 mOsmol to about 40 mOsmol.

14. The method of claim 1, wherein high shear mixing is not required to uniformly distribute the drug within the vehicle.

15. The method of claim 1, wherein the vehicle comprises a consistency index of about 400 to about 30,000 at a shear rate of about 1 $sec^{-1}$.

16. The method of claim 1, wherein the starch comprises hydrated starch granules.

17. The method of claim 1, wherein vehicle comprises at least about 70% by weight of the aqueous medium.

18. The method of claim 1, wherein the drug is a solid dosage form that is ground to a powder and then admixed with the vehicle.

19. A method of administering a drug to a patient, comprising preparing a drug in an oral dosage form according to claim 1 and orally administering the oral dosage form to the patient.

* * * * *